US006386759B2

(12) United States Patent
Noettling

(10) Patent No.: US 6,386,759 B2
(45) Date of Patent: May 14, 2002

(54) X-RAY DIAGNOSTIC DEVICE HAVING A SUPPORTING APPARATUS

(75) Inventor: Alois Noettling, Pottenstein (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/739,160

(22) Filed: Dec. 18, 2000

(30) Foreign Application Priority Data

Dec. 17, 1999 (DE) .......................................... 199 61 098

(51) Int. Cl.⁷ ................................................. A61B 6/04
(52) U.S. Cl. ........................ 378/209; 378/208; 378/20
(58) Field of Search .......................... 378/209, 20, 196, 378/208

(56) References Cited

U.S. PATENT DOCUMENTS

| 4,618,133 A | * 10/1986 | Siczek ............................ 5/601 |
| 5,454,884 A | * 10/1995 | Kirmse et al. .............. 378/209 |
| 5,764,719 A | 6/1998 | Noettling |
| 6,095,685 A | * 8/2000 | Tamura ....................... 378/208 |

FOREIGN PATENT DOCUMENTS

| DE | 19 95 093 | 10/1968 |
| DE | 69 38 432 | 3/1971 |
| DE | 295 04 285 | 8/1996 |
| DE | 195 09 007 | 9/1996 |
| DE | 195 09 009 | 10/1996 |

* cited by examiner

*Primary Examiner*—David P. Porta
*Assistant Examiner*—Therese Barber
(74) *Attorney, Agent, or Firm*—Schiff Hardin & Waite

(57) ABSTRACT

An X-ray diagnostic device has a supporting apparatus for the object being examined, a signal processing device for producing a tomogram or a three-dimensional image of the object being examined and a reproductive apparatus for displaying the tomogram or three-dimensional image. The supporting apparatus has a supporting plate with a movement device for the supporting plate in order to move the plate about an axis of rotation with the movement angle being greater than 10° and the movement device has both a drive device and a sensor for detecting the movement of the supporting plate about the axis of rotation.

20 Claims, 6 Drawing Sheets

X-RAY DIAGNOSTIC DEVICE HAVING A SUPPORTING APPARATUS

BACKGROUND OF THE INVENTION

The present invention is directed to a support device for an X-ray diagnostic device.

Widely differing supporting apparatus for an object being examined are known which allow X-ray images of the object being examined to be produced in conjunction with an X-ray diagnostic appliance. For example, it is known for a supporting plate to be arranged on a movable carriage on which the object being examined can be supported for an X-ray examination. Furthermore, X-ray diagnostic appliances are known which are in the form of an appliance above or below a table and have an associated supporting apparatus with a supporting plate for an object being examined. The supporting plate can be moved along its longitudinal axis and/or its transverse axis and/or about a pivoting axis and/or in elevation with respect to the floor of an examination room, for widely differing examinations. The recording unit, which comprises a beam transmitter and a beam receiver, may either be fixed in position, or else may be movable, for example in the direction of the longitudinal axis of the supporting plate, or may be moved about the longitudinal axis in conjunction with a C-curve, so that projections from different directions are feasible. Furthermore, X-ray diagnostic appliances are known whose recording unit comprises a beam transmitter and a beam receiver. The beam transmitter and the beam receiver may, in this case, be movably decoupled from one another or coupled via separate holding means so that, for example, X-ray examinations can also be carried out on a standing patient.

U.S. Pat. No. 5,764,719, which is incorporated herein by reference thereto and which claims priority from German 195 09 007.1; German 195 09 009 C1 and German Gebrauchsmuster 295 04 285 U1, disclose X-ray diagnostic appliances which have a signal processing device by means of which it is possible to produce tomogram images or three-dimensional images of an object being examined. In these X-ray diagnostic appliances, a recording unit comprises a beam transmitter and a beam receiver is once again provided, and has an associated supporting apparatus for an object being examined. Relative movement between the recording unit and the supporting apparatus allows the beam to scan the object being examined. The relative movement in this case covers an angle of more than 180° about a vertical axis.

German Gebrauchsmuster 19 95 093 U1 describes a rotating patient cradle for X-ray appliances, which comprises two strands which are driven by electric motors and have rotary plates to which the rotating cradle is fitted such that it can be removed.

A rotating patient cradle for X-ray appliances is known from German Gebrauchsmuster 69 38 432 U1, in which the rotating cradle or a table plate is optionally attached and detached by means of a base frame and holding means.

SUMMARY OF THE INVENTION

The object of the invention is the further advantageous refinement of a supporting apparatus for an X-ray diagnostic appliance, in particular with respect to producing tomogram and/or three-dimensional images using the X-ray diagnostic appliance.

According to the invention, the object is achieved by an X-ray diagnostic appliance or device having a supporting apparatus for an object being examined, a signal processing device for producing images selected from tomogram images and three-dimensional images and a reproduction device for displaying the images, said supporting apparatus comprising a supporting plate being mounted for movement about a rotational axis through a movement angle greater than 10°, and a movement device for moving the plate, said movement device including a drive device and a sensor for detecting the movement of the supporting plate about the rotational axis.

The advantage of the X-ray diagnostic device according to the invention is, in particular, the capability to use a movement device to move the supporting plate of the X-ray diagnostic device through a movement angle of more than 10° about the rotation axis. Such a supporting apparatus is suitable for use to produce and reproduce tomogram or three-dimensional images of the object being examined by means of the X-ray diagnostic device, in which the associated supporting apparatus can produce the required rotation of the object being examined about a rotation axis. It is thus possible to produce tomogram or three-dimensional images even with X-ray diagnostic appliances whose recording unit is in a fixed position. With X-ray diagnostic appliances whose recording unit position is variable, tomogram images can even be produced if the recording unit can only be moved through an angle of less than 180° around the object being examined. The sensor allows the movement of the supporting plate about the rotation axis to be detected, so that the tomogram or three-dimensional images can be calculated by means of the signal processing device or unit.

Further advantages and details of the invention are evident from the following description of an exemplary embodiment, the drawings and claims.

DESCRIPTION OF THE PREFERRED EMBODIMENT

Figure 1:
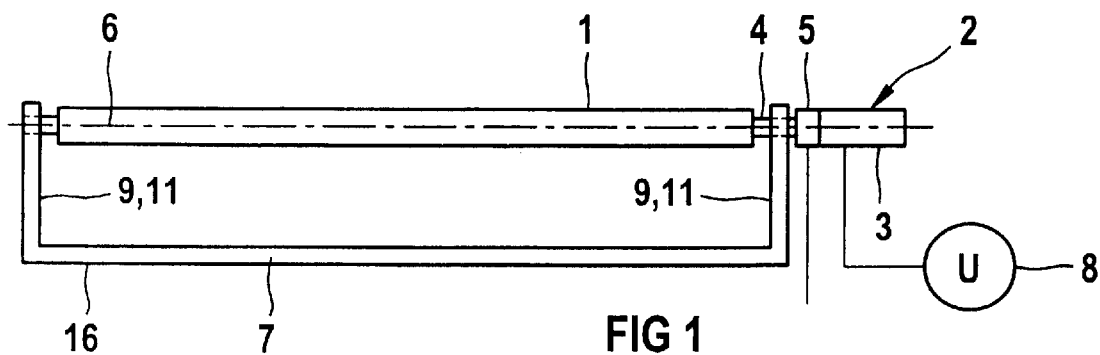
FIG. 1 is a side view of a first exemplary embodiment of a supporting apparatus according to the present invention.

The principles of the present invention are particularly useful when incorporated in a supporting apparatus (see FIG. 1) for supporting an object being examined for an X-ray diagnostic appliance, which supporting apparatus has a supporting plate 1 for the object being examined and a movement device 2 for the supporting plate 1. The movement device 2 has a drive device 3 whose speed and position are controlled, for example an electromechanical device, in particular an electric motor, whose output drive or shaft 4 is connected to the supporting plate 1. Furthermore, an angular position sensor 5 is provided, which detects the pivoting of the supporting plate 1 about a rotation axis or axis of rotation 6 and produces signals which are suitable for detecting the position in which the supporting plate 1 is located. It is evident from this exemplary embodiment that the supporting plate 1 is supported by a frame 7. The supporting apparatus can thus be arranged via the frame 7 on a chassis or on a supporting apparatus or a supporting plate associated with the X-ray diagnostic appliance. Actuation of the drive device 3, for example using a voltage source 8, allows the supporting plate 1 to be moved about the rotation axis 6 so that an object being examined and arranged on the supporting plate 1 can be scanned by a beam, in particular in a cross-sectional plane, in conjunction with a recording device comprising a beam transmitter and a beam receiver. The signals from the angular position sensor and from the beam receiver are supplied, while the beam is being scanned, to a signal processing device, which will be explained later, so that a tomogram image can thus be produced on a display device.

Figure 2:
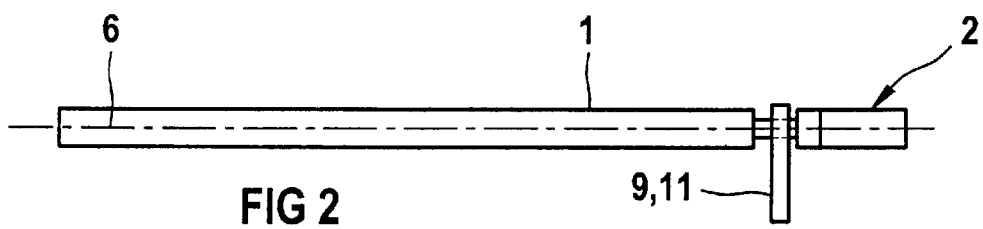
FIG. 2 is a side view of a second exemplary embodiment of a supporting apparatus according to the invention.

FIG. 2 shows another or second exemplary embodiment of a supporting apparatus but in which, in contrast to the supporting apparatus shown in FIG. 1, the supporting plate 1 is supported on only one end face via a frame or a base, for example a U-shaped bracket or a plate 9 (FIG. 3) which, for example, have an opening 10 for the output drive or shaft 4. The supporting plate 1 may thus be attached to a base frame of a carriage, to a stand, in particular to a stand associated with the X-ray diagnostic appliance, or to a supporting plate associated with the X-ray diagnostic appliance, with generally known attachment means, such as screws, catch connections or plug-in connections, being suitable for this purpose.

Figure 3:
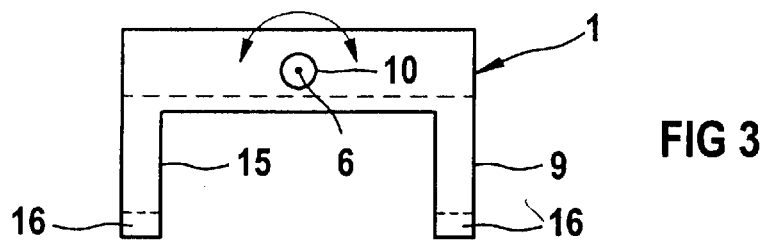
FIGS. 3 and 4 are end views of exemplary embodiments of a support for the supporting apparatus as shown in FIG. 1 or 2.
Figure 4:
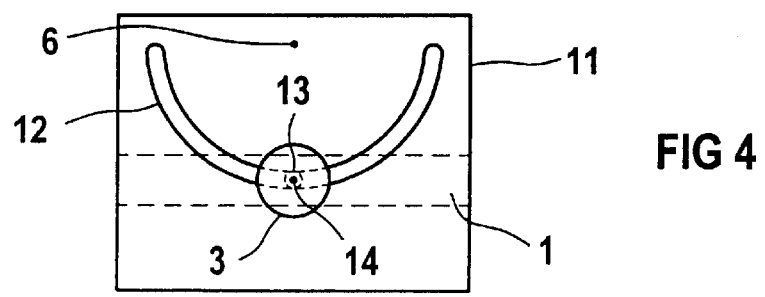

FIG. 4 shows a further plate 11 as a frame or base member which has a curved guide 12 on which a support 13 for the supporting plate 1 can be moved. The supporting plate 1 can thus be moved via a drive device 3, as shown in FIGS. 1 and 2, both about the rotation axis 6 and about the longitudinal axis 14 of the supporting plate 1. In this case, it is clear that the longitudinal axis 14 and the rotation axis 6 can be offset parallel to one another. In the exemplary embodiments shown in FIGS. 1–4, the supporting plate 1 is designed so that it extends in a plane. It is thus self-evident that attachment means or locking means must be provided for the object being examined, in order to prevent this object from falling off the supporting plate 1 when the supporting plate 1 is being moved about the rotation axis 6. As an alternative to this, the supporting plate 1 may also be in the form of a shell, thus allowing better guidance, positioning and retention of the object being examined. Obviously, it is preferable for the supporting plate 1 to be designed such that it is transparent to the beams. If the frame 7, as shown in FIG. 3, is designed not only as a plate 9, but as shown in FIG. 1, then it can be supported by its lower edges 16 on a frame associated with the X-ray diagnostic appliance, or on an associated supporting plate. In this case, there is then essentially no need for transparency for the beams and, in particular, this also reduces the costs. In this case, attachment means must, of course, be provided, by means of which the frame 7 can be attached to the associated frame or the associated supporting plate. Catch or bolt connections are particularly suitable for this purpose, since they allow rapid attachment and positioning, as well as rapid separation.

Figure 5:
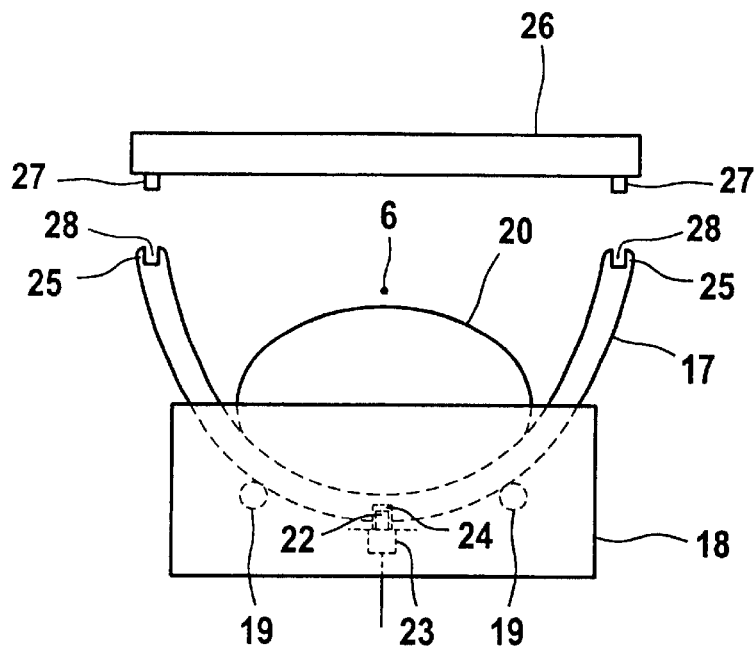
FIG. 5 is an end view of a third exemplary embodiment of a supporting apparatus according to the invention.

FIG. 5 shows a further or third exemplary embodiment of a supporting apparatus according to the invention, which has a supporting plate 17 in the form of a curved shell. The supporting plate 17, which is in the form of a shell, is supported on the base 18, for example via rollers 19, so that it can be moved along its circumference, so that an object being examined which is supported on the supporting plate 17 which is in the form of a shell can be moved about the rotation axis 6. In conjunction with the supporting plate 17, the base 18 may, in this case, form a separate supporting apparatus, or else may be part of a supporting apparatus associated with the X-ray diagnostic appliance. If the rollers 19 can be driven via an electromechanical drive, then this allows movement about the rotation axis 6. In order to prevent the supporting plate 17 from being moved inadvertently about the rotation axis 6, it is possible to provide a locking device which, for example, as a pin 22 in conjunction with an electromagnet 23, which prevent movement of the supporting plate 17 when appropriately actuated such that the pin 22 engages in a recess 24 in the supporting plate 17. Alternatively, the supporting plate may also be in the form of a curved supporting plate base and may be supported on the frame 7, 9 or 11, for example via rollers 19, such that it can be moved at least along a subregion of its circumference. Thus, the plate or shell 17 is supported at its two ends.

It can also be seen from FIG. 5 that a planar supporting plate 26 can also be arranged on the longitudinal edges 25 of the supporting plate 17, and this planar supporting plate 26 has, for example, pins 27 which engage in recesses 28 in the edges 25 of the supporting plate 17. Such a planar supporting plate 26 allows simpler access to the object being examined. The planar supporting plate 26 may extend not only in a plane, as shown, but may also have a curved region which is tangential to at least a portion of the object being examined. When above-table X-ray diagnostic appliances are being used with this embodiment, it may be advantageous to provide an opening for the beam receiver in the supporting plate 17, so that it is possible to reduce the distance between the object being examined and the beam receiver by inserting the latter into the opening. This opening can be closed by a cover when using the supporting plate 17.

Figure 6:
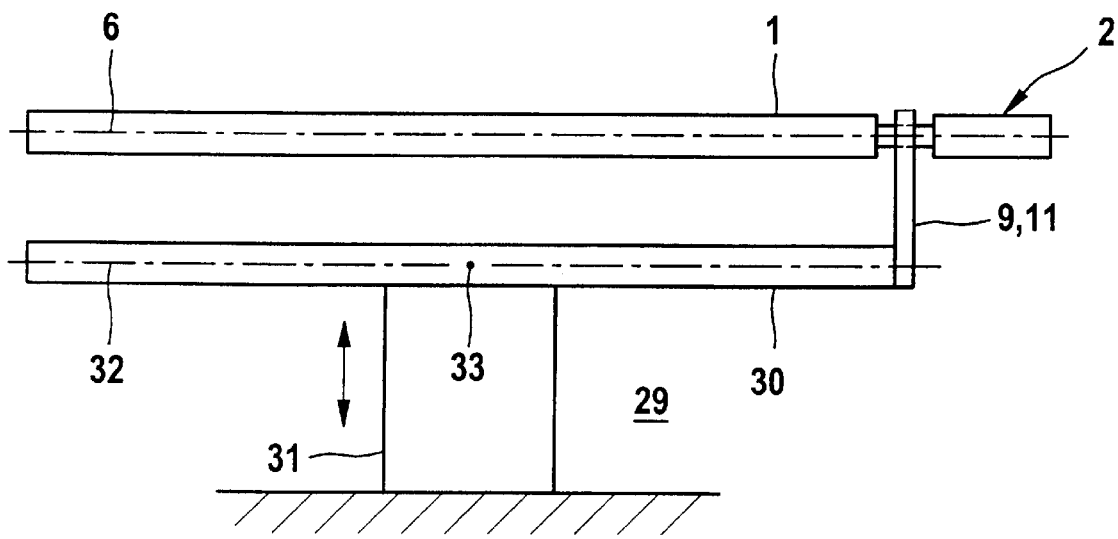
FIG. 6 is a side view of a supporting apparatus according to the invention in conjunction with a supporting plate which is supported on a stand.

A supporting apparatus which is associated with an X-ray diagnostic appliance is denoted, in principle, by the reference symbol 29 in FIG. 6 and has a supporting plate 30 which is associated with the X-ray diagnostic appliance and is supported on a stand 31. This supporting plate 30 may be supported on the stand 31 so that it can be moved along its longitudinal axis 32 and/or in a direction at right angles to this longitudinal axis 32, that is to say along the transverse axis of the supporting plate 30, and/or about a pivoting axis 33 and/or so that its height can be changed, that is to say the distance to the floor. It is furthermore evident from FIG. 6 that a supporting apparatus as shown in FIG. 1 or 2 can be arranged on the supporting apparatus 29 which is associated with the X-ray diagnostic appliance, in particular on the associated supporting plate 30.

Figure 7:
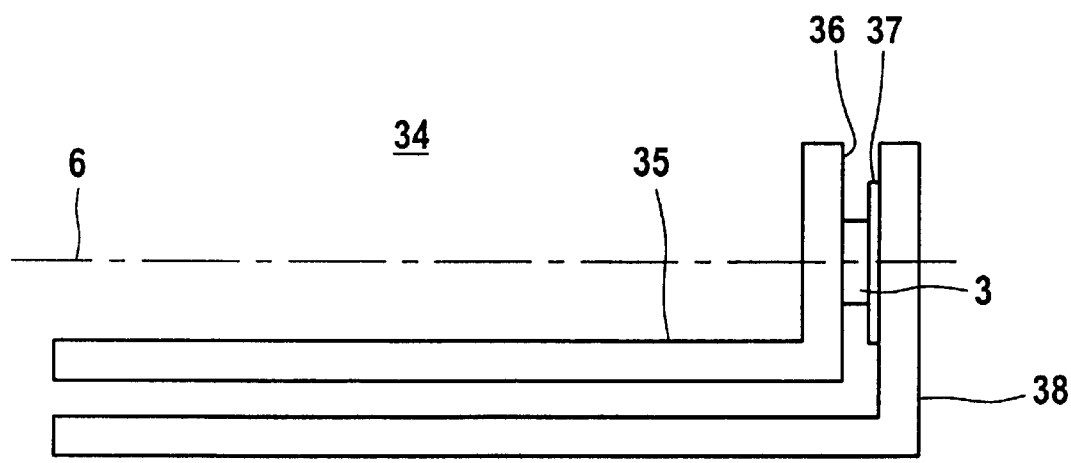
FIG. 7 is a side view of a fourth exemplary embodiment of a supporting apparatus according to the invention in conjunction with a further supporting plate.

FIG. 7 shows another supporting apparatus 34 according to the invention which, for example, has an L-shaped supporting plate 35 whose short limb 36 is connected to a drive device 3. The L-shaped supporting plate 35, and thus an object being examined, can be moved about the rotation axis 6 via the drive device 3. The supporting apparatus 34 can be connected via a foot part 37, which is connected to the drive device 3, to a supporting plate 38 which is associated with the X-ray diagnostic appliance. The plate 38 is, for example, L-shaped and is arranged on a stand that is not shown.

Figure 8:
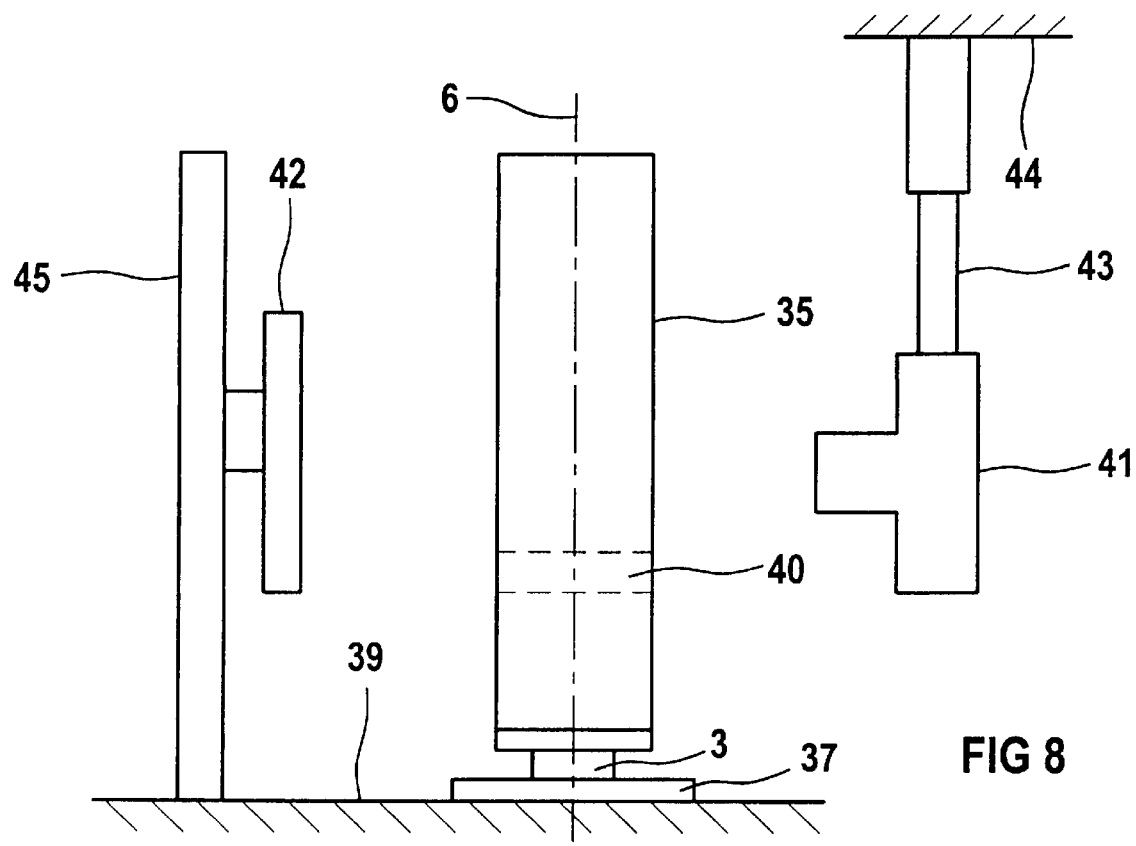
FIG. 8 is a side view of a supporting apparatus according to the invention in conjunction with a recording unit comprising a beam transmitter and a beam receiver.

It is evident from FIG. 8 that the supporting apparatus 34 can be arranged, via its foot part 37, on the floor 39 of an examination room. An object being examined and standing on the short limb 36 can thus be moved about the rotation axis 6 via the drive device 3. A dashed line is used to show that a seat plate 40, which extends at right angles to the supporting plate 35 and parallel to the limb 36, can also be arranged on the L-shaped supporting plate 35, so that examinations are also possible when the object being examined is seated. The supporting plate 35 may, in this case, be composed of just one material, for example CFC; however, it may also have different materials, for example with the long limb being composed of a material which is transparent to the beams, and the short limb being composed of metal. A beam transmitter 41 and a beam receiver 42 are provided for scanning the beam of the object being examined. The beam transmitter 41 is arranged, for example, via a vertical support 43 on the ceiling 44 of the examination room. However, this could likewise also be arranged on the floor 39 or on a wall of the examination room. The beam receiver 42 is supported, for example, on a column 45 so that it can be moved at least in elevation, that is to say its distance from the floor can be changed. For this purpose, the column 45 can be arranged on the floor 39, on the ceiling 44 or on a wall, and may also be supported so that it can be moved in three dimensions. The beam receiver 42 is designed so that electrical signals which are dependent on beam shadowing of the object being examined originate from it and are supplied to the signal processing device, which will be explained later. The beam receiver 42 may, for example, be in the form of an image intensifier video chain or a solid object detector.

Figure 9:
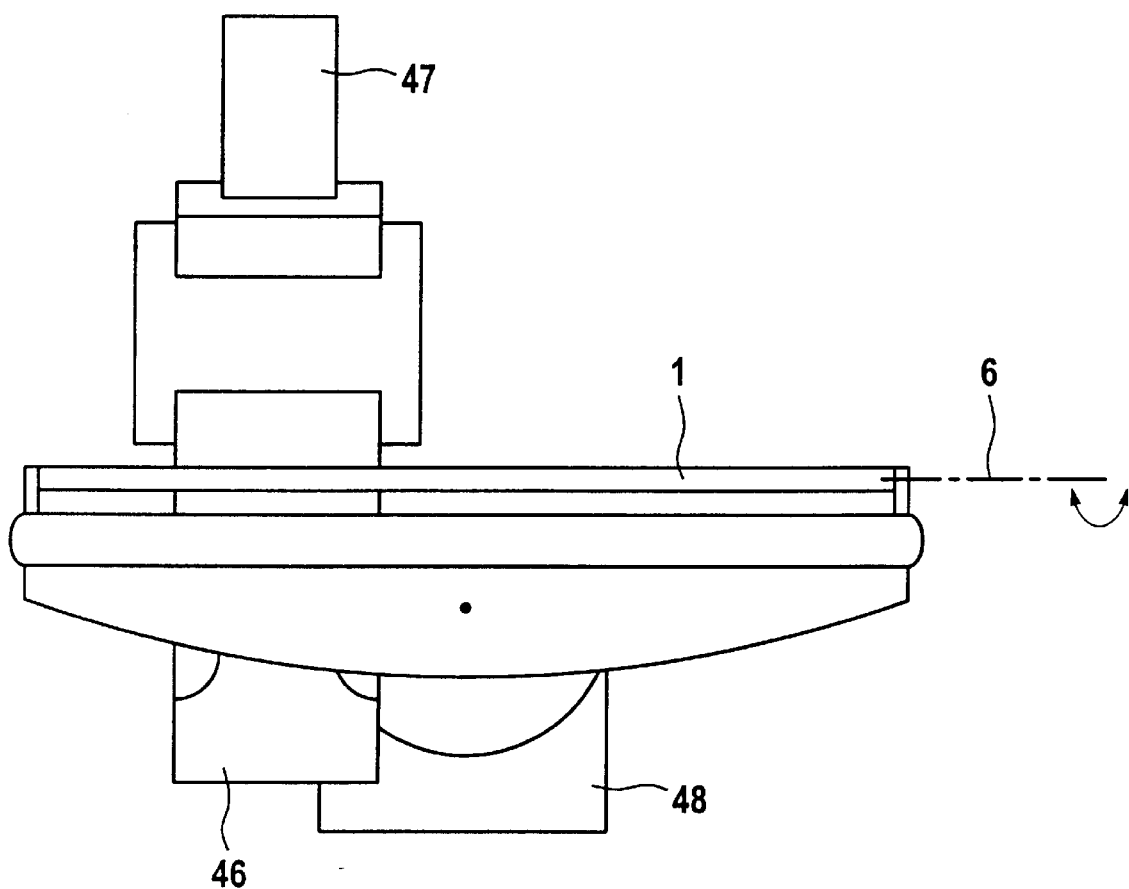
FIG. 9 is a side view of an X-ray diagnostic appliance having a supporting apparatus according to the invention.

An under-table X-ray diagnostic appliance is shown as an example in FIG. 9. This under-table X-ray diagnostic appliance has a recording unit comprising a beam transmitter 46 and a beam receiver 47. Furthermore, a supporting plate 1 is provided on which an object being examined can be arranged. Such an X-ray diagnostic appliance which is known per se is designed, according to the invention, with a supporting apparatus 48 which allows the supporting plate 1 to be moved about a rotation axis 6, with the supporting apparatuses illustrated in FIGS. 1, 2, 5 and 7 being suitable, by way of example, for this purpose. Furthermore, the supporting apparatus 48 may also be designed such that it allows relative movement between the recording unit and the supporting plate 1 and/or movement of the supporting plate 1 along its longitudinal and/or its transverse axis and/or pivoting about a horizontal axis. The recording unit may be fixed in position with respect to a frame of this X-ray diagnostic appliance, or else may also be movable on a holder about a central axis, for example the rotation axis 6.

Figure 10:
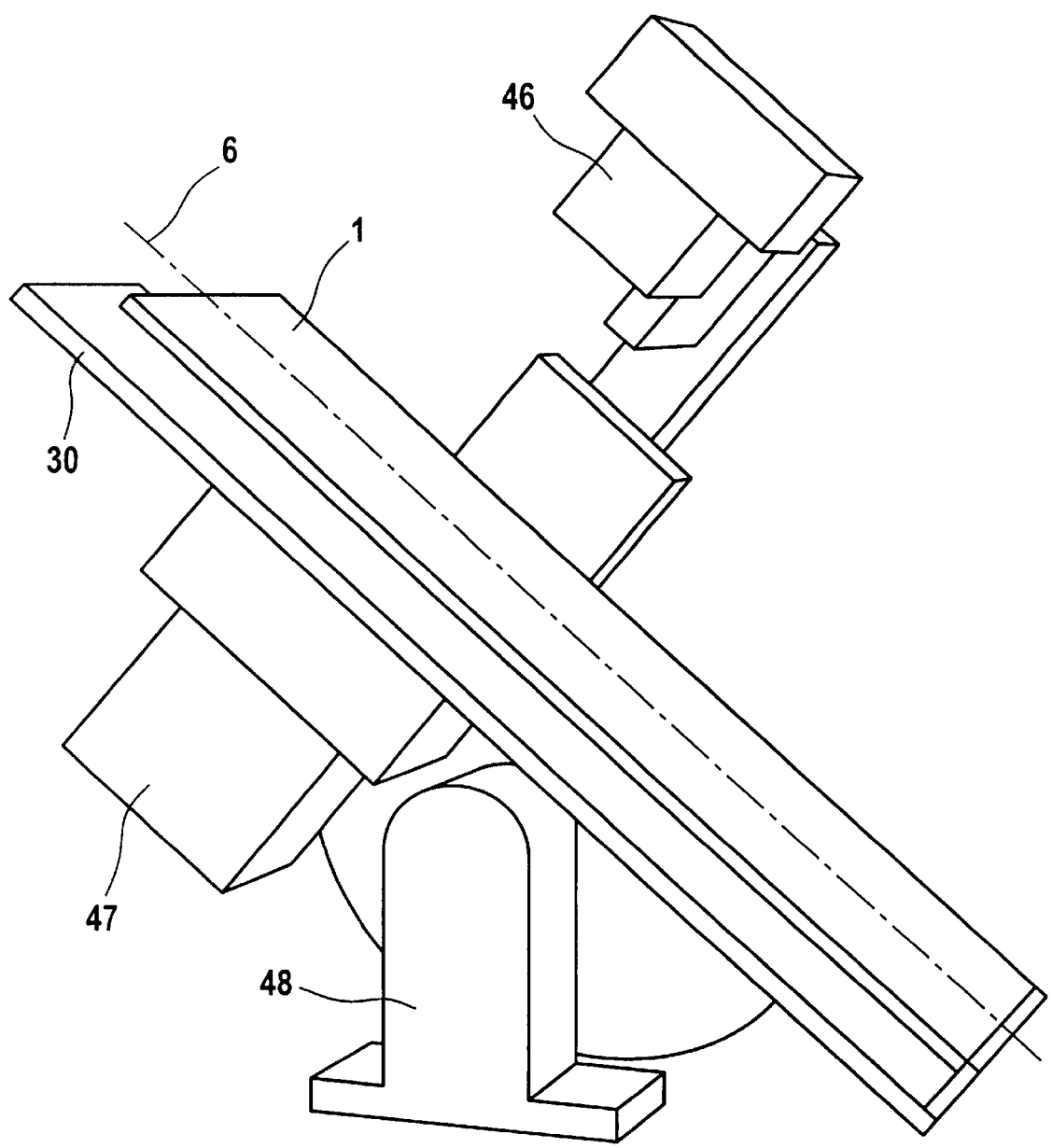
FIG. 10 is a side view of a second exemplary embodiment of an X-ray diagnostic appliance having a supporting apparatus according to the invention.

FIG. 10 shows an above-table X-ray diagnostic appliance in which, in contrast to the X-ray diagnostic appliance shown in FIG. 9, the beam receiver 47 is arranged underneath the supporting plate 1, and the beam transmitter 46 is arranged above the supporting plate 1. In this case as well, the supporting apparatus maybe designed either as a separate part, as shown in FIGS. 1, 2, 5 and 7, and arranged on a frame associated with the X-ray diagnostic appliance or on an associated supporting plate, or the supporting plate which is associated with the X-ray diagnostic appliance is supported such that it can move about the rotation axis 6.

Figure 11:
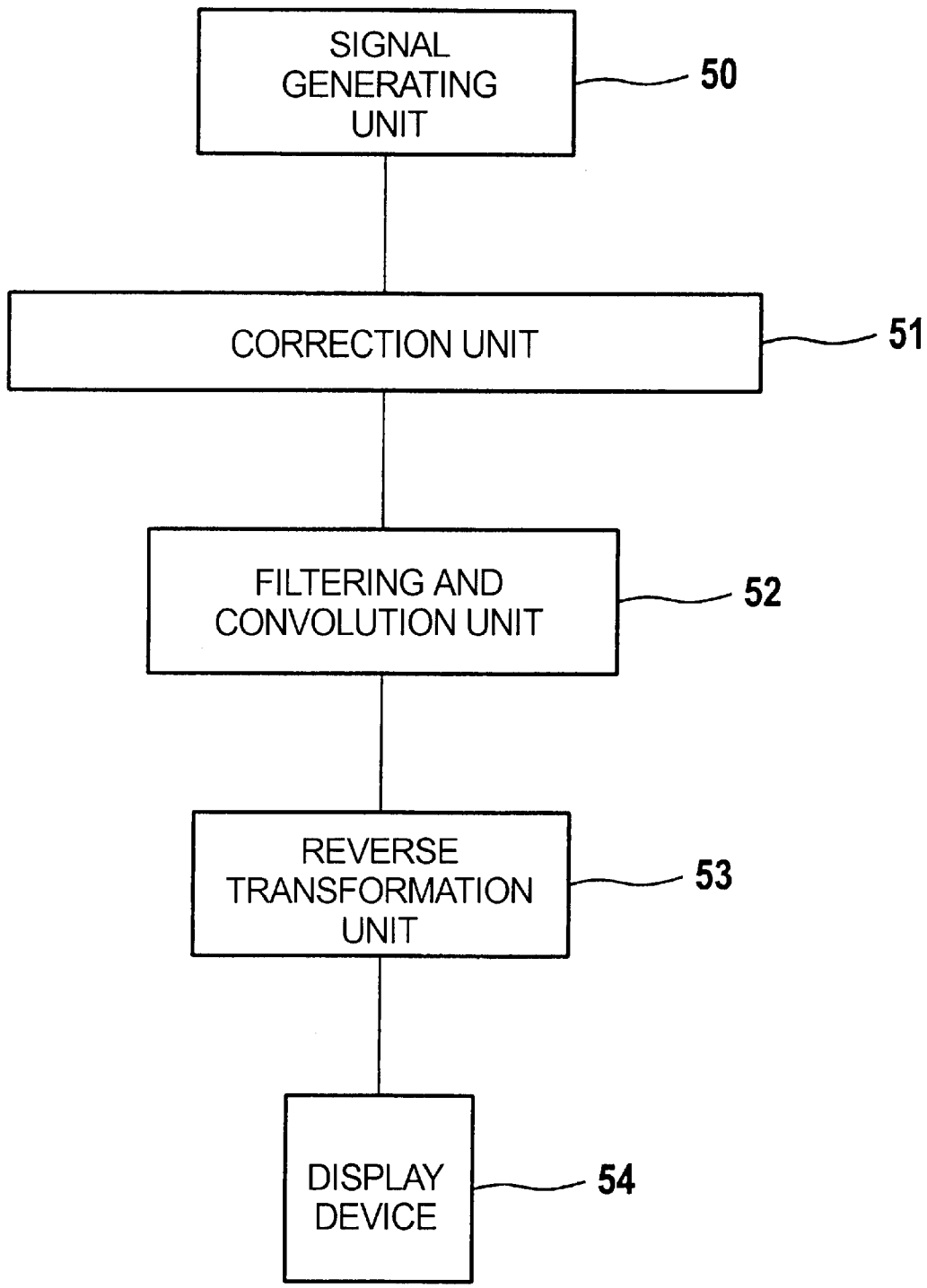
FIG. 11 is a block diagram of a signal processing device for an X-ray diagnostic appliance as shown in FIG. 8, 9 or 10.

FIG. 11 shows a signal processing device 49 of an X-ray diagnostic appliance in the form of a block diagram, by means of which it is possible to produce tomogram or three-dimensional images of an object being examined from the electrical signals which can be derived from the beam receiver 42 or 47. The reference symbol 50 denotes a signal generating unit or device, which produces signals based on the beam shadowing produced during the beam scanning of the object being examined. These signals are supplied to a correction unit or device 51, in which the signals are processed to correct for vignetting and/or geometric distortion and/or appliance deflection and, for signal calculation, the film (beam receiver) focal length, the projection angle, the position of the central rotation point and the $I_0$ correction, and in which three-dimensional signals corresponding to the beam scanning are produced. In a further unit 52, these signals are subjected to filtering and convolution and are supplied to a fourth unit 53, in which reverse transformation of the signals is carried out. The signals emerging from the fourth unit 53 can be supplied to a visualization unit 54, for example a display device, so that a tomogram image representative or a three-dimensional image representation of the area scanned by the beam is possible.

Although the supporting plates illustrated by way of example are not fitted with any apparatuses for fixing the object being examined, it is obvious that such apparatuses should be provided. For example, cut-outs can be incorporated in the supporting plate, into which fastening straps can be inserted in order to fix the object being examined. Likewise, arms can be provided which can pivot and enclose the object being examined. Alternatively or additionally, handles or openings can be provided in order to give the object being examined, for example a patient, something to grip.

Since, for imaging, it is highly important to determine or know the central rotation point or the rotation axis or other parameters of the recording geometry, beam-absorbent markings can be provided on the supporting plate 1, which are imaged in the X-ray image and with whose aid this information can be determined. This information can either be determined or checked whenever beam scanning is carried out, or it can be detected once and stored in a memory. It is then worthwhile to carry out a repeated calibration or determination process at regular time intervals. Further details relating to this can be found, in particular, in the documents cited initially.

Although various minor modifications may be suggested by those versed in the art, it should be understood that I wish to embody within the scope of the patent granted hereon all such modifications as reasonably and properly come within the scope of my contribution to the art.

I claim:

1. An X-ray diagnostic device having a supporting apparatus for an object being examined, a signal processing device for producing an image selected from a tomogram image and three-dimensional images of the object being examined and a reproduction apparatus for displaying the images, the supporting apparatus comprising a supporting plate, and a movement device for the supporting plate in order to move the plate about an axis of rotation with the movement angle being greater than 10°, said movement device having a drive device and a sensor for detecting the movement of the supporting plate about the axis of rotation.

2. An X-ray diagnostic device according to claim 1, wherein the axis of rotation is an axis selected from a longitudinal axis of the supporting plate and an axis extending parallel to the longitudinal axis of the supporting plate.

3. An X-ray diagnostic device according to claim 1, wherein the supporting plate is supported on a frame and the frame can be fitted by attachment means to a supporting apparatus which is associated with the X-ray diagnostic appliance.

4. An X-ray diagnostic device according to claim 3, wherein the frame has at least a curved guide, and the longitudinal axis of the supporting plate can be moved along said guide.

5. An X-ray diagnostic device according to claim 4, wherein the frame can be fitted to a stand and can be moved along one of the longitudinal axis, the traverse axis, a combination of the transverse and longitudinal axis and can be elevated.

6. An X-ray diagnostic device according to claim 1, wherein an end face of the supporting plate is supported so that the plate can be moved about the axis of rotation.

7. An X-ray diagnostic device according to claim 1, wherein the supporting plate has an L-shaped cross-section in the direction of the axis of rotation.

8. An X-ray diagnostic device according to claim 1, wherein the supporting plate has the form of a curved shell and wherein the supporting plate is supported so that it can be moved at least along a sub-region of a circumference of the shell on rollers which are provided on a base, so that the supporting plate can be moved about the axis of rotation.

9. An X-ray diagnostic device according to claim 8, which includes means for locking the supporting plate and for blocking movement about the axis of rotation.

10. An X-ray diagnostic device according to claim 8, wherein a separate supporting plate which extends essentially in a plane is mounted on the curved shell of the supporting plate to enclose the object being examined.

11. An X-ray diagnostic device according to claim 10, wherein the separate supporting plate is fitted on longitudinal edges of the curved shell by attachment means which are provided.

12. An X-ray diagnostic device according to claim 1, wherein the supporting plate is attached to the frame by a supporting plate base and the supporting plate base is curved and can be moved on supporting means along at least a sub-region of its circumference.

13. An X-ray diagnostic device according to claim 1, wherein the X-ray diagnostic appliance has a directly associated supporting apparatus for an object being examined and the supporting apparatus and the directly associated supporting apparatus can be connected to one another.

14. An X-ray diagnostic device according to claim 1, wherein the X-ray diagnostic appliance has a fixed position recording unit comprising a beam transmitter and a beam receiver and wherein the supporting apparatus can be moved through an angle of more than 180° about the axis of rotation.

15. An X-ray diagnostic device according to claim 1, wherein the X-ray diagnostic device has a beam transmitter and a beam receiver and wherein the beam transmitter and the beam receiver are decoupled so that the supporting apparatus is in the form of a separate unit and wherein the supporting plate and the recording unit formed by the beam transmitter and the beam receiver can be moved relative to one another in such a manner that the relative movement angle is greater than 180°.

16. An X-ray diagnostic device according to claim 1, wherein the supporting plate can be moved through an angle of more than 180° about the axis of rotation.

17. An X-ray diagnostic device according to claim 1, wherein the X-ray diagnostic appliance has a beam transmitter and a beam receiver which are located opposite one another and can be moved about a central axis via a holder.

18. An X-ray diagnostic device according to claim 1, wherein the signal processing device can be supplied with the signals from the beam receiver of the X-ray diagnostic device and wherein the signal processing device is designed to produce a tomogram image of a cross-sectional plane of the object on display from the signals from the beam receiver.

19. An X-ray diagnostic device according to claim 1, wherein the beam transmitter of the X-ray diagnostic device is designed to produce a conical beam and wherein the signal processing device is designed to produce a graphical representation of a three-dimensional image of an examination area of the object being examined from the signals from the beam receiver on the display device.

20. An X-ray diagnostic device having a supporting apparatus for an object being examined, a signal processing device for producing an image selected from a tomogram image and three-dimensional images of the object being examined and a reproduction apparatus for displaying the images, the supporting apparatus comprising a supporting plate, and a movement device for the supporting plate in order to move the plate about an axis of rotation with the movement angle being greater than 10°, said movement device having a drive device and a sensor for detecting the movement of the supporting plate about the axis of rotation, said sensor having an output connected to the signal processing device.

* * * * *